(12) United States Patent
Busby

(10) Patent No.: US 7,874,999 B2
(45) Date of Patent: Jan. 25, 2011

(54) DETECTING ACCESS DISCONNECT USING NEEDLE SLEEVE

(75) Inventor: Donald Busby, Tampa, FL (US)

(73) Assignees: Baxter International, Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 617 days.

(21) Appl. No.: 11/860,052

(22) Filed: Sep. 24, 2007

(65) Prior Publication Data

US 2009/0082647 A1 Mar. 26, 2009

(51) Int. Cl.
*A61M 37/00* (2006.01)
*A61M 5/32* (2006.01)
*A61B 5/00* (2006.01)

(52) U.S. Cl. .................. 604/6.16; 604/192; 600/309

(58) Field of Classification Search ....... 604/4.01–6.16, 604/192, 198, 177, 263, 264, 272; 600/300, 600/309; 210/600, 634, 645, 646, 649–651
See application file for complete search history.

(56) References Cited

U.S. PATENT DOCUMENTS

| | | | |
|---|---|---|---|
| 5,549,571 A * | 8/1996 | Sak | ............................ 604/198 |
| 6,530,911 B1 | 3/2003 | Utterberg | |
| 6,596,234 B1 | 7/2003 | Schnell et al. | |
| 6,974,473 B2 | 12/2005 | Barclay et al. | |
| 2005/0038325 A1* | 2/2005 | Moll | ........................... 600/300 |
| 2005/0113756 A1 | 5/2005 | Goh | |
| 2005/0124938 A1 | 6/2005 | Yang | |
| 2005/0277861 A1 | 12/2005 | Anthony | |
| 2008/0065006 A1 | 3/2008 | Roger | |
| 2008/0195021 A1 | 8/2008 | Roger | |
| 2008/0195060 A1 | 8/2008 | Roger | |
| 2009/0079578 A1 | 3/2009 | Dvorsky | |
| 2009/0080757 A1 | 3/2009 | Roger | |
| 2009/0082646 A1 | 3/2009 | Bouton | |
| 2009/0082649 A1 | 3/2009 | Muller | |
| 2009/0082653 A1 | 3/2009 | Rohde | |
| 2009/0082676 A1 | 3/2009 | Bennison | |
| 2009/0088612 A1 | 4/2009 | Bouton | |
| 2009/0088613 A1 | 4/2009 | Marttila | |
| 2009/0088683 A1 | 4/2009 | Roger | |
| 2009/0105627 A1 | 4/2009 | Rohde | |
| 2010/0022934 A1 | 1/2010 | Hogard | |
| 2010/0022935 A1 | 1/2010 | Muller | |

FOREIGN PATENT DOCUMENTS

| | | |
|---|---|---|
| DE | 4432348 A1 | 2/1995 |
| EP | 1736185 A2 | 12/2006 |
| WO | 2008/066106 | 6/2008 |

* cited by examiner

*Primary Examiner*—Leslie R Deak
*Assistant Examiner*—Philip R Wiest
(74) *Attorney, Agent, or Firm*—K&L Gates LLP

(57) ABSTRACT

An access needle for extracorporeal therapy is equipped with a mount and a sleeve having a metal or magnetic component at its distal end. The mount includes a sensor for detecting when the distal end is pressed against the mount. The sensor is a hall-effect sensor or a proximity sensor. When therapy is begun, the sleeve is rolled up and urged against the mount, exposing the needle for use with the patient. While the sleeve, and the piece of metal or magnet, remains in contact with the sensor, the needle has not been dislodged and therapy may continue. If the needle is dislodged, the sleeve pushes away from mount, moving the metal or magnet away from the sensor. The sensor notes the dislodgement and sends a signal to alert the patient or a caregiver.

19 Claims, 8 Drawing Sheets

DETECTING ACCESS DISCONNECT USING NEEDLE SLEEVE

BACKGROUND

The invention is in the field of medical treatments generally and patient vascular access systems. The present invention relates to embodiments of a method and a system for detecting a needle disconnect during extracorporeal blood treatment or other medical procedure.

The maxim of "first, do no harm," may be a good summary of the Hippocratic oath required of doctors and practiced by medical professionals. Nowhere is this principle required more than in modern medicine. With patients living longer, there are more extended treatments and more frail patients than ever. Such patients are in danger from complications that can arise from continuing therapeutic procedures, and even from diagnostic procedures, that are necessary for their continued care. Treatments involving extra-corporeal blood treatment are clear examples.

The most obvious danger is infection, but the harm caused by infection can be overcome by not re-using even supposedly-sterile devices and by diligent attention by the patient himself or herself, and by care givers attending to the patient. Other dangers also arise, but, like infections, have been difficult to eradicate. One of these dangers arises in blood treatment procedures in which the blood of a patient is physically removed from the patient for treatment, and then returned, all in the same procedure. Removal and return of blood is practiced in hemodialysis, for those persons whose kidneys do not function well. Other procedures, such as apheresis, involve removing blood from a patient or a donor to separate blood platelets or plasma from the red blood cells and then returning the red blood cells to the patient or donor, as described in U.S. Pat. Nos. 5,427,695 and 6,071,421.

The extracorporeal medical treatments described above require that the blood be removed for treatment and then returned. This requires access to the patient's vascular system, from which blood is removed and to which blood is then returned. If a "batch" treatment is used, that is, a quantity of blood is withdrawn, treated and returned, only a single needle is used. Each batch of such treatment is typically short, and the treatment is attended by a medical professional at a clinic or hospital. A variation on the batch treatment is a "batch" continuous method in which only a single needle is used. There are distinct withdraw and return phases in a batch continuous process. During the draw phase, blood is processed and additional blood is sent to a holding container to be processed during the return phase. In the return phase, blood is processed from the holding container and then returned to the patient or donor through the single needle. Other treatments are continuous, such as the platelet separation discussed above, or dialysis treatment, and may require a duration of several hours or even overnight.

Continuous treatments require two needles, or access points, one for withdrawal of blood and one for return. The withdrawal site is normally an artery, and a needle and a pump are used to provide the blood to the therapeutic machine. It is relatively simple to detect a problem with withdrawal, for instance, if the withdrawal needle is dislodged, using conventional air sensor technology. Detecting a problem in the return of the blood to the patient is more difficult. The return line typically includes a needle with venous access. If the return line is dislodged, the blood is not returned to the patient's vascular system, but may continue to be pumped and may accumulate near the patient. Depending on the pumping rate of the blood and the time for treatment, this could have life-threatening effects on the patient within a very short period of time.

Accordingly, a number of apparatuses have been devised for detecting needle dislodgement, especially venous needle dislodgement. An example is U.S. Pat. Appl. Publ. 2006/0130591. In a device according to this application, a venous needle is equipped with a photosensor and is covered with an opaque patch. This device would not send a signal or an alarm if the needle begins leaking or is only slightly dislodged. For example, the photosensor could still fail to detect light because the needle has not been dislodged sufficiently to expose the photosensor to light. In addition, this method requires ambient light and would thus not be suitable for patients that cover their arm with a blanket or who perform nocturnal dialysis while sleeping in a dark bedroom.

Numerous other techniques have been devised, many of them depending on a flow of blood causing conductivity between two electrodes or two wires. What is needed is a better way of quickly detecting dislodgement of a venous or other needle from a patient, so that inadvertent loss of blood and harm to the patient is avoided.

SUMMARY

One embodiment is a method of detecting a needle disconnection. The method includes steps of providing a needle having a mount with a sensor and a sleeve with a metallic target, the sensor configured for detecting the metallic target, placing the needle into an extracorporeal blood processing access site, urging the sleeve against the mount, thereby placing at least a portion of the metallic target near the sensor, taking a reading of the sensor after the metallic target is urged against the mount, monitoring the access site by taking additional readings of the sensor during an extracorporeal blood processing therapy, and sending a signal if a reading consistent with absence of the target from the sensor is detected, thereby indicating dislodgement of the needle.

Another embodiment is a method for detecting needle disconnection at an access site. The method includes steps of providing an access needle with an electroactive sleeve and a sensor on a mount of the access needle, wherein the sensor is configured to detect metal or a magnet on the sleeve, mounting the access needle on the access site of a patient and pressing the sleeve toward the mount, taking a reading of the sensor with the pressed sleeve, monitoring the access site during a therapy procedure by taking additional readings with the sensor, and sending a signal if a reading indicative of needle dislodgement is taken.

Another embodiment is a system for detecting needle dislodgement. The system includes an access needle suitable for mounting near an access site for extracorporeal therapeutic blood processing, the access needle including a mount, a sleeve having an electromagnetic target, the sleeve positioned over the needle and adjacent the mount, a sensor on the mount for detecting the electromagnetic element, and a communications circuit in communication with the sensor, wherein the needle is configured for placing into the access site, the sleeve is configured for pressing against the mount, the sensor is configured for detecting the electromagnetic element, and the communications circuit is configured for sending data indicative of a position of the electromagnetic element with respect to the sensor.

Another embodiment is a system for detecting needle dislodgement. The system includes a needle with a mount suitable for mounting near an access site for an extracorporeal blood therapy, a sleeve having a metallic or magnetic target, the sleeve positioned over the needle and adjacent the mount, a sensor on the mount for detecting the metallic or magnetic target, and a control circuit connected to the sensor, wherein the needle is configured for placing into the access site, the sleeve is configured for pressing against the mount, and the control circuit is configured for taking readings of the sensor indicative of a position of the metallic or magnetic target with respect to the sensor.

Additional features and advantages are described herein, and will be apparent from, the following Detailed Description and the figures.

DETAILED DESCRIPTION

Figure 1:
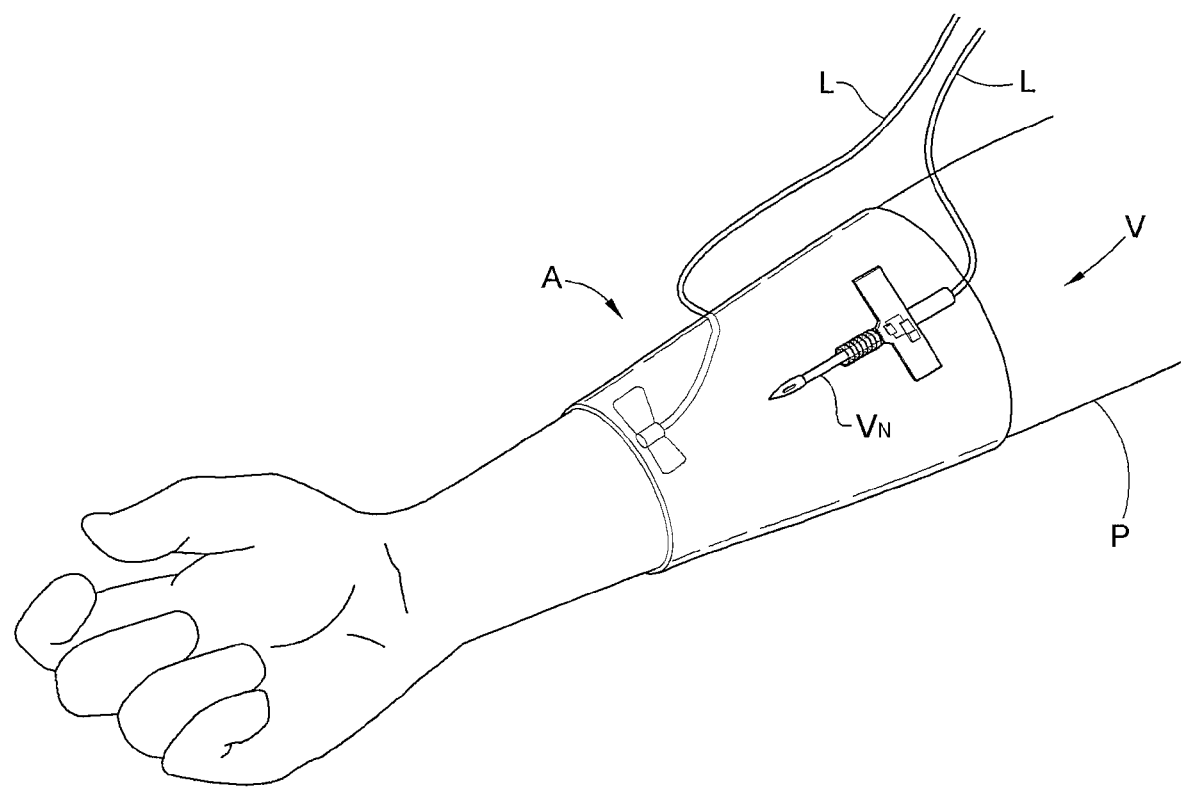
FIG. 1 is a prior art depiction of a fistula access site for a hemodialysis patient.

There are many embodiments of an access needle with a sleeve and a sensor that is capable of detecting needle dislodgement, as will be discussed below. Access needles are typically used in extracorporeal blood therapies, such as hemodialysis or apheresis. An access site is typically on a patient's upper arm or lower arm, as depicted in FIG. 1. A patient's arm P includes an arterial access site A for sending blood to the therapy machine, and a venous access site V for returning the blood to the patient. The venous access site includes a venous access needle, $V_n$. Blood lines L and tubing connect the patient to the therapy machine.

Figure 2A:
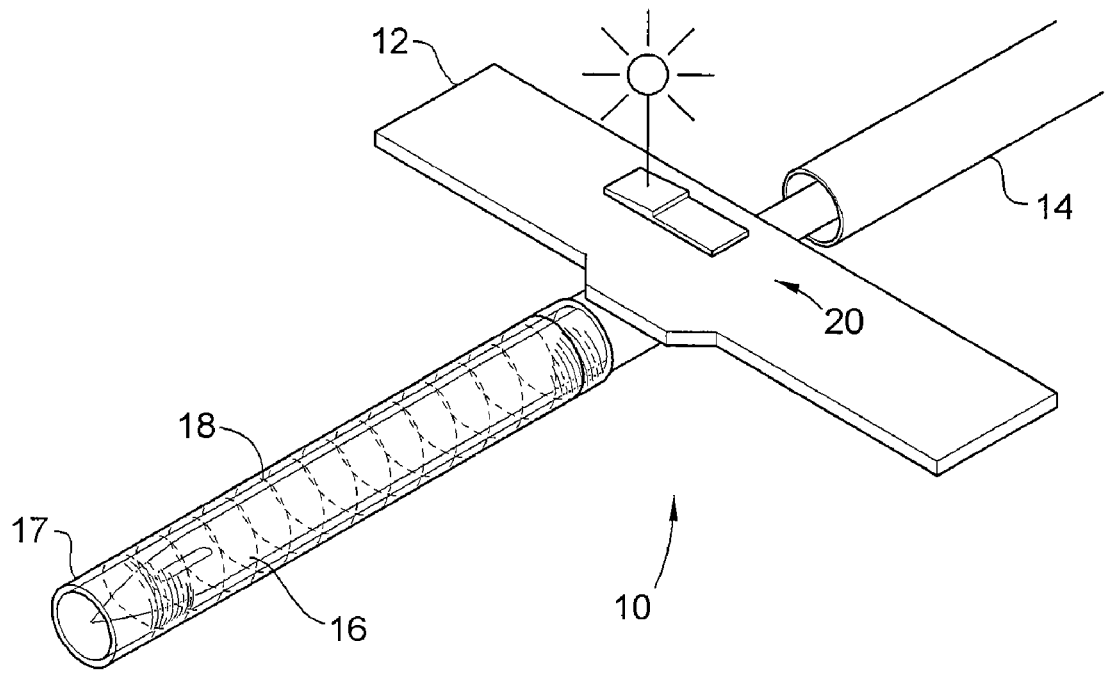
FIGS. 2A-2B depict a first embodiment of a needle with an electroactive sleeve.
Figure 2B:
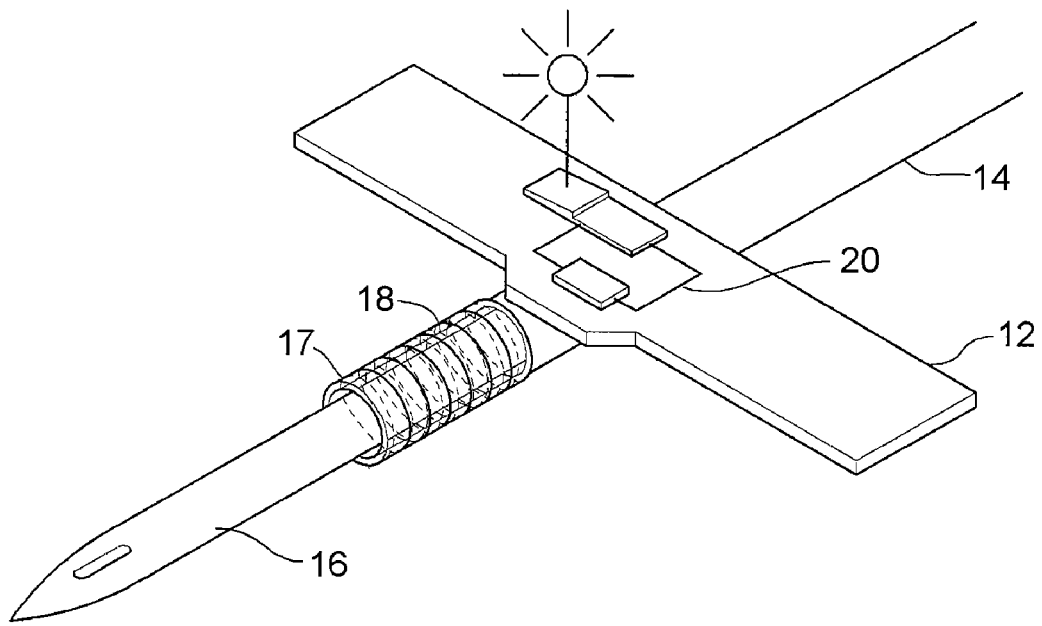

A first embodiment is disclosed in FIGS. 2A-2B. An access needle assembly 10 includes a butterfly mount 12, tubing 14, a venous access needle 16, a sleeve 17 made from clear tubing, and an embedded wire 18. The wire may be steel wire or may be magnet wire, which is primarily a copper alloy. The embedded wire is in the shape of a helix, wound within the tubing. The wire may be uniformly wound, or may be wound with extra turns at the distal end, the end away from the mount. The mount 12 includes a detector circuit 20 to detect the wire within the tubing. The sleeve is an electroactive sleeve, that is, a plastic or elastomeric sleeve containing a metallic or magnetic component that is detectable by a proximity or hall-effect sensor.

FIG. 2A depicts the access needle assembly as it appears before the needle is implanted within a venous access site. Tubing 14 covers the needle to protect the patient and caregivers, including clinic or hospital staff, or home care workers, from needle sticks. The mount is intended to attach firmly to the patient, typically by being taped down, and of course the needle is attached to tubing 14 for connection to the therapy machine. The tubing is attached by a luer or other connection between the patient tubing and the needle. At this point, the sensor is remote from most of the wire. Thus, the sensor reading before installation into the patient, a baseline or initial reading, may be considered as a reading indicative of the wire being away from the sensor, while will later be interpreted as a dislodgement of the needle from the site.

FIG. 2B then depicts the access needle assembly as it appears after insertion into a patient venous access site. Mount 12 is secured to the patient, typically with adhesive tape or straps. As needle 16 is inserted into the patient, sleeve 17 is rolled back to expose the needle, and the sleeve is urged against mount 12 and held there while the needle is in place in a vein or fistula of the patient. Wire 18 in the sleeve is also urged against the mount and held close to detector circuit 20 on the mount. Thus, the wires embedded in the sleeve also become bunched up against the mount and detector circuit with a sensor for detecting the presence of the wire. At this point the detector strongly indicates the presence of the wire or other metallic or magnetic material place on the distal end of sleeve 17. This may be considered to be a second baseline or initialization reading, indicative of proper placement of the needle, with the wire in contact with the sensor.

When therapy is proceeding normally, sleeve 17 and wires 18 remain rolled up near the sensor. If the needle is dislodged, however, the sleeve springs back from the sensor, and the wire is no longer detected, or at least is no longer detected to the same extent as when it was urged against the sensor. The patient or a caregiver can then be alerted to the danger, or the therapy machine or other device can be programmed to cease therapy immediately in order to safeguard the patient. The sensor may operate at any reasonable frequency, that is, readings per minute. A rate of about 1 check per second, that is, about 1 Hz, is sufficient for patient safety. Most proximity or other sensors can far exceed this rate by operating in the kilohertz range. Some capacitive sensors take a little longer for successive readings, but should be capable of at least 50 Hz, that is, 50 checks per minute on whether the metal or magnet is still detected.

The sleeve is a polymeric material that is resilient and able to be formed around a metallic or magnetic component. Thus, polyethylene, polypropylene, PVC or other plastic material may be used. The sleeve is not in contact with blood, because the sleeve is pushed away from the needle during use. Thus, there is no danger from leaching of plasticizer during the therapy. Elastomers may also be used, such as silicone or urethane. Thus, the sleeve may be made from any plastic or elastomeric material suitable for medical use. The sleeve should be sufficiently thick to protect the patient and caregivers from needle sticks, and should be flexible, so that the sleeve is easily pushed away from the needle and against the mount. The sleeve may be from 0.005 to 0.0030 inches thick, or it may be from 0.010 to 0.020 inches thick (wall thickness). Other thicknesses may be used. The sleeve should have sufficient thickness and resiliency so that when the needle becomes dislodged, the previously rolled-up or folded sleeve will unroll or unfold, and move the piece of metal or magnet away from the sensor. The sleeve may be molded around wire, as noted, such as metallic wire or magnet wire.

It is not necessary that the sleeve contain a metal or magnetic material along its entire length. The element that the sensor detects need only be at the distal end of the sleeve, so that the sensor can detect when the distal end of the sleeve is close or adjacent. Thus, rather than a spiral wire embedded along the length of the sleeve, a metal washer may be molded into the distal end of the sleeve. Alternatively, a thin circular magnet may be adhered outside the distal end of the sleeve, so that the magnet or the washer is held close to the sensor when the access needle is properly placed. The metal or magnet is considered a target for detection by the sensor. In one embodiment, the target is shaped like a washer, i.e., a thin cylinder. In another embodiment, the target is shaped like a portion of a washer, that is, a thin arc or metal or a magnet having an arc shape. Other embodiments may use a thin strip of a magnet or piece of metal having another shape.

Figure 3:
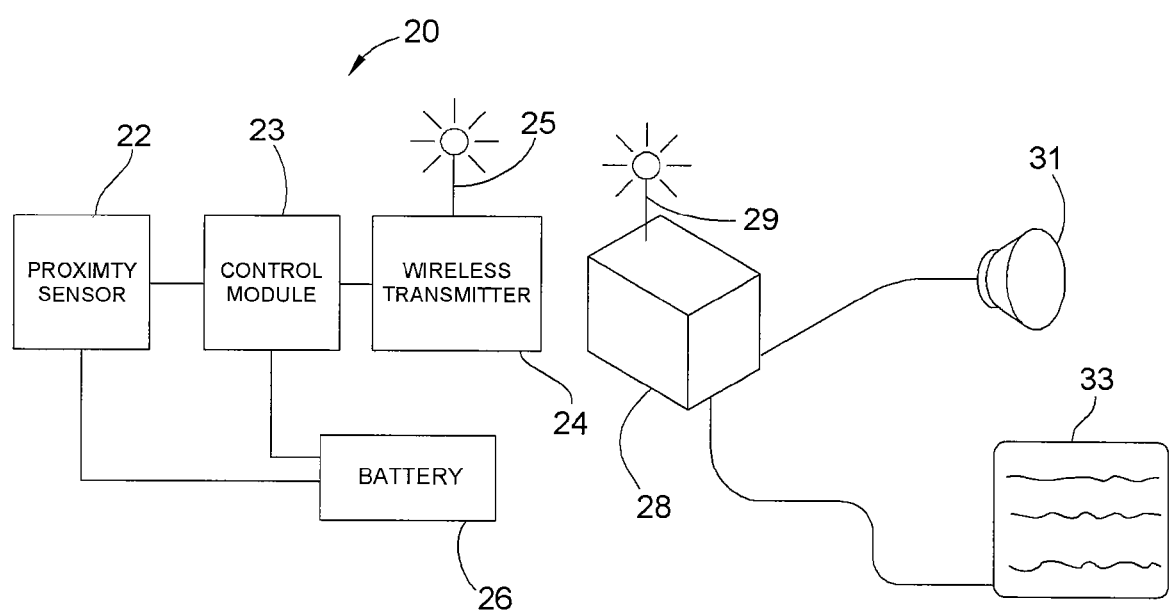
FIG. 3 is a schematic depiction of a circuit for interfacing with the electroactive sleeve embodiment of FIGS. 2A-2B.

The detector circuit 20 is detailed in FIG. 3. In one embodiment, the detector circuit 20 includes a proximity sensor 22, a controller for the proximity sensor and a communications module 24. The communications module 24 is a wireless transmitter with an antenna 25. A battery 26 provides a power source for the circuit. The communications module sends signals indicative of its findings or readings to a remote receiver 28 and antenna 29. One module that works is a wireless module in accord with ZigBee/IEEE 805.15.4. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). The remote receiver may be part of a therapy machine, or may be a stand-alone circuit for receiving the signals and then alerting the patient or caregiver by with a local output device, such as a speaker 31 or a video screen 33.

The proximity sensor may be any suitable sensor for detecting the presence of wire in the tubing. For instance, inductance or capacitance sensors, suitable for sensing the presence of steel or copper wiring, may be used. Such sensors are manufactured by Allegro MicroSystems, Inc., Worcester, Mass., and Melexis Microelectronic Systems, Concord, N.H., U.S.A. Many sensors are sold with internal circuitry that converts the actual detected signal directly into a usable DC output, such as 0 to 5 volts or 4-20 mA, depending on whether an object is or is not sensed. The sensor is connected to a control module, such as a sensor controller. These may be very simple circuits, capable of detecting a voltage or current, or may be more complex circuits, including analog-to-digital converters and signal processing circuitry, with a supervisory microcontroller to interpret the signals and decide, using software, of appropriate action to take when the signal detected by the proximity sensor changes.

Thus, in one embodiment, proximity sensor 22 includes merely a power supply 26 and an ADC converter to convert analog signals from the sensor, which converted signals are then sent through the communications module 24 to a remote receiver for processing and logic. In another embodiment, the control module includes an ADC converter, a microcontroller and a memory, and a computer program for comparing a reading from the sensor to a baseline reading or more than one baseline reading. The comparison, and a look-up table in the memory, enables the microcontroller to decide whether the sensor reading is normal, i.e., the proximity sensor presently detects the metal embedded in the tubing. If the sensor readout is not normal, the controller may be programmed to send a signal through the communications module to alert the patient or a caregiver. The signal may be to alert the caregiver, to cease therapy, or may be to sound an alarm through a local output device, such as a speaker 31 or a video screen 33.

Figure 4A:
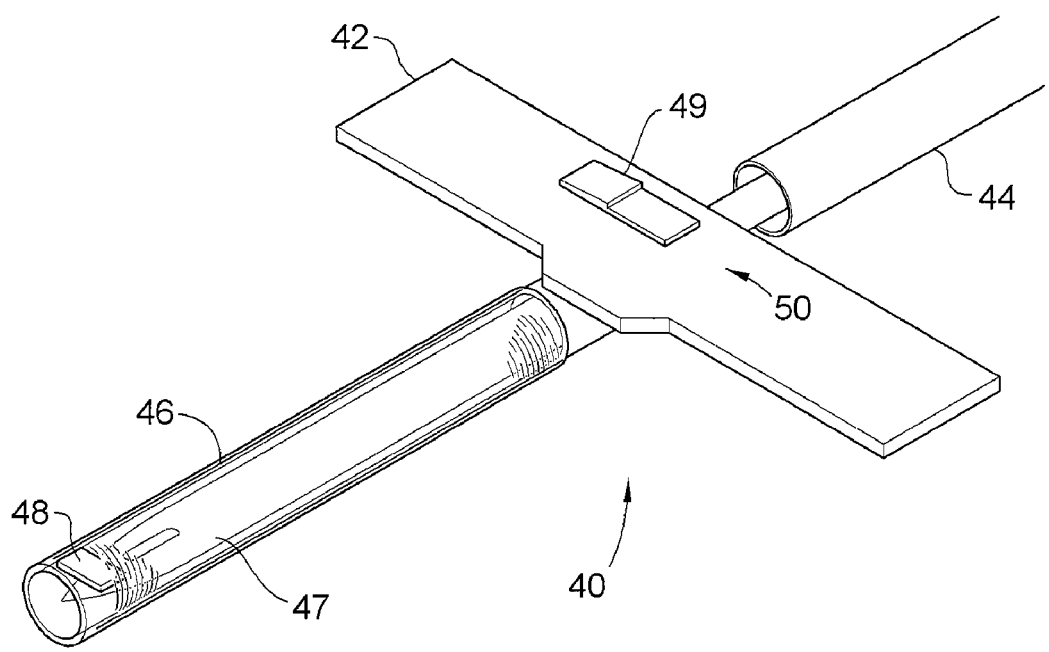
FIGS. 4A-4B depict a second embodiment of an electroactive sleeve.
Figure 4B:
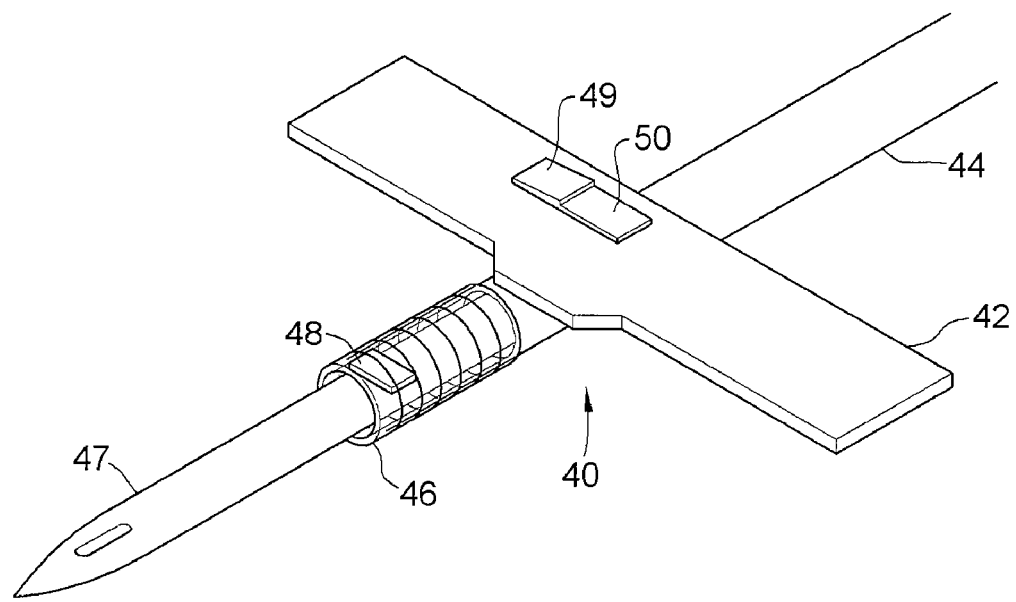

There are other embodiments of a needle disconnect detector. FIGS. 4A-4B disclose uninstalled and installed depictions of the detector. In FIG. 4A, the detector system 40 includes a mount 42, tubing 44 for connection to the therapy machine, and a venous access needle 47. Needle 47 includes a magnet 48 at the distal end of needle sleeve 46. The detector system 49 and a communications module 50 are mounted on mount 42. In other embodiments, the magnet is a piece of metal, such as a magnetic or non-magnetic piece of steel.

FIG. 4B depicts the detector 40 when the needle has been installed in a patient. Mount 42 is affixed firmly to the patient, with adhesive tape or medically-approved devices, such as straps. As the needle is placed into the vein, sleeve 46 is rolled up against the mount 42. Magnet 48 nears hall-effect sensor 49 and control circuit 50. A current is generated by the presence of magnet 48 in the vicinity of the Hall-effect sensor and its magnetic field. The current is greater when the magnet is close to the sensor, and the current is less when the magnet moves away. A circuit in the control module may use this varying current directly or may convert the current to a voltage signal. Before installation, the magnet is far away from the sensor, and the sensor does not detect the magnet. The "no magnet" baseline reading may be used as one limit of detection of the hall effect sensor. When the needle is installed, the magnet is near the sensor, and the sensor gives a reading indicative of the presence of the magnet. This "magnet present" reading may also be taken as an opposite baseline reading. A limit may be set between these two readings as an indication of when the magnet has moved away from the detector, and by implication, when needle disconnect has occurred. The control circuit, such as a controller, may then decide when the limit has been reached and then send a signal as a result of the change in detection reading.

Figure 5:
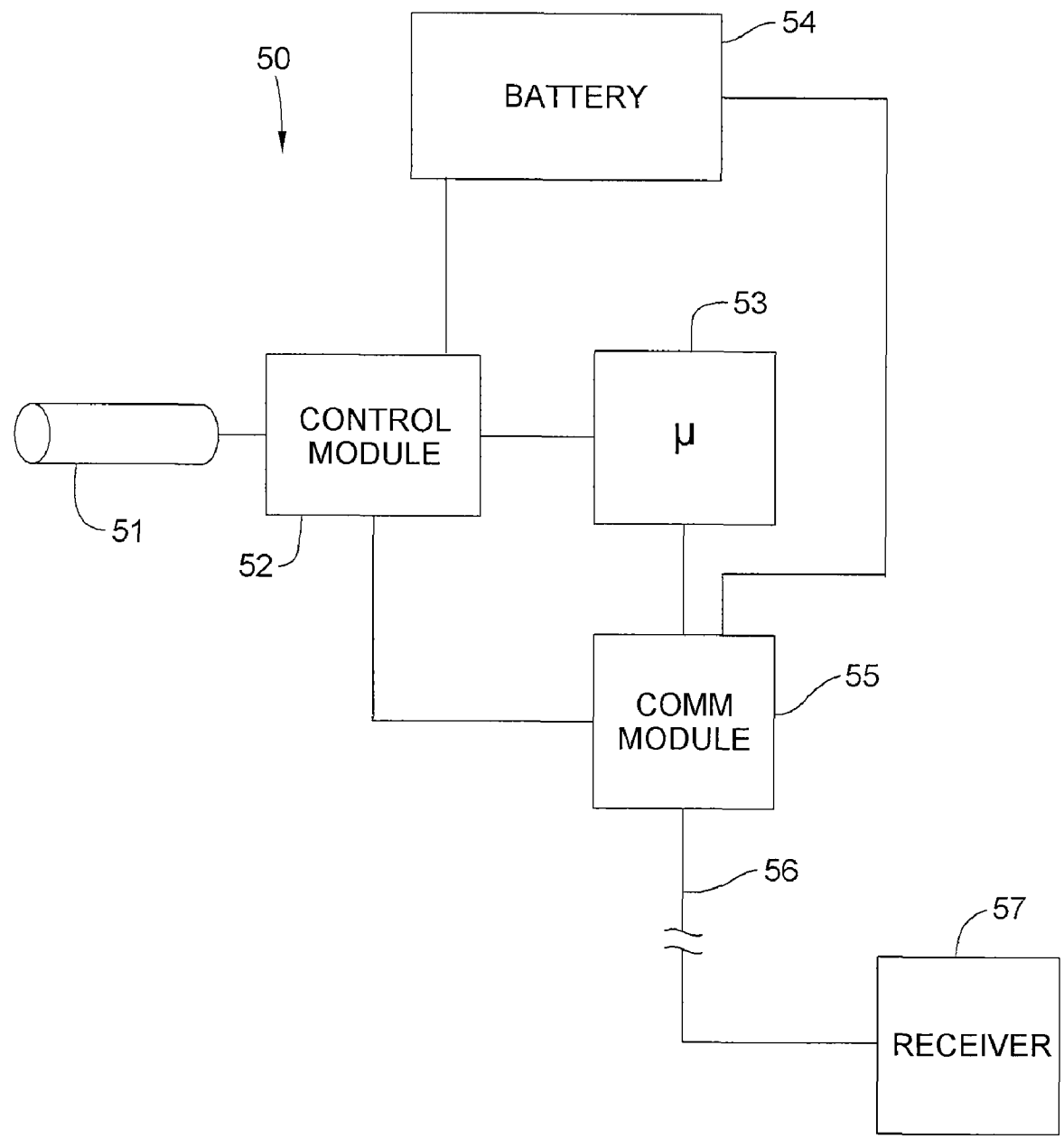
FIG. 5 is a schematic depiction of a circuit for interfacing with the electroactive sleeve embodiment of FIGS. 4A-4B.

A more complicated control scheme with these elements is depicted in FIG. 5. Proximity sensor 51 is connected to control module 52 and microcontroller 53. A battery 54 supplies power to the microcontroller and the control module. The microcontroller is also in communication with a communication module 55. In this embodiment, the communications module communicates with a remote receiver 57 via a cable 56. The receiver may be part of a therapy machine or may be a stand-alone receiver. Cable 56, in this embodiment, extends from the controller and mount on the patient to the therapy machine or other receiver, which is nearby, within a few feet of the patient.

Figure 6:
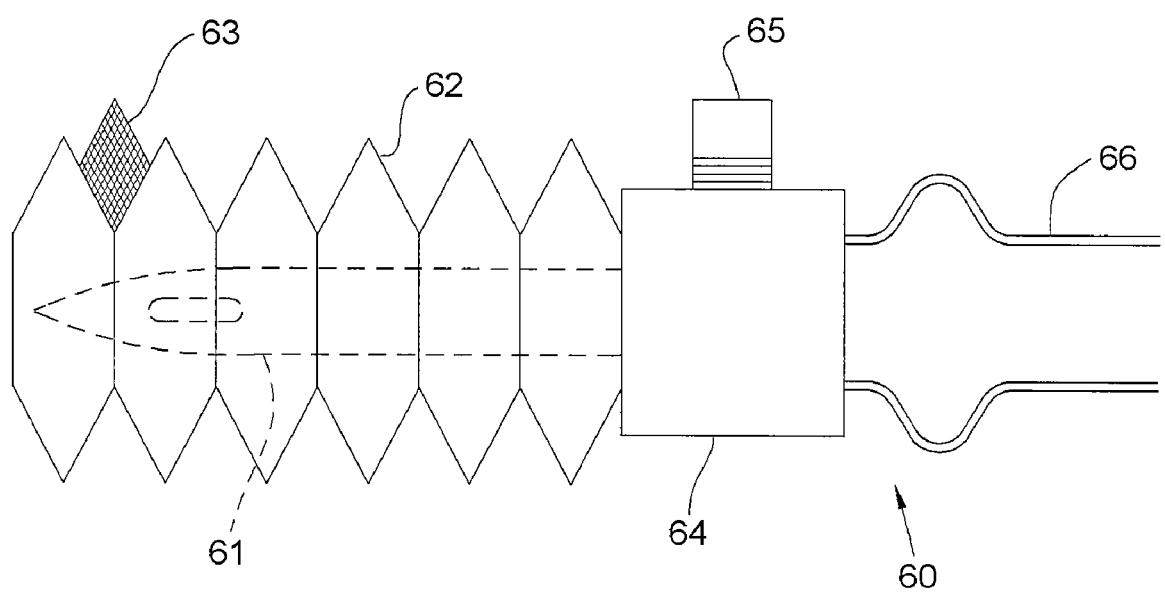
FIG. 6 is another embodiment of an access needle with a sleeve having a metallic or magnetic component.

Another embodiment 60 of an access needle with an electroactive sleeve is depicted in FIG. 6. In this embodiment, the sleeve 62 is in the form of a bellows. The bellows may be made from materials as noted above for sleeve tubing, that is, any medically acceptable plastic or elastomer. The sleeve covers access needle 61 which is embedded in mount 64. The sleeve includes a small magnet 63 near the distal end of the sleeve. Sensor 65 is placed on mount 64, along with any necessary power or communication elements for alerting the patient or caregiver if the sensor does not detect the magnet once therapy has begun. Mount 64 also includes an interface 66 for blood tubing. The interface may be a connector.

Figure 7:
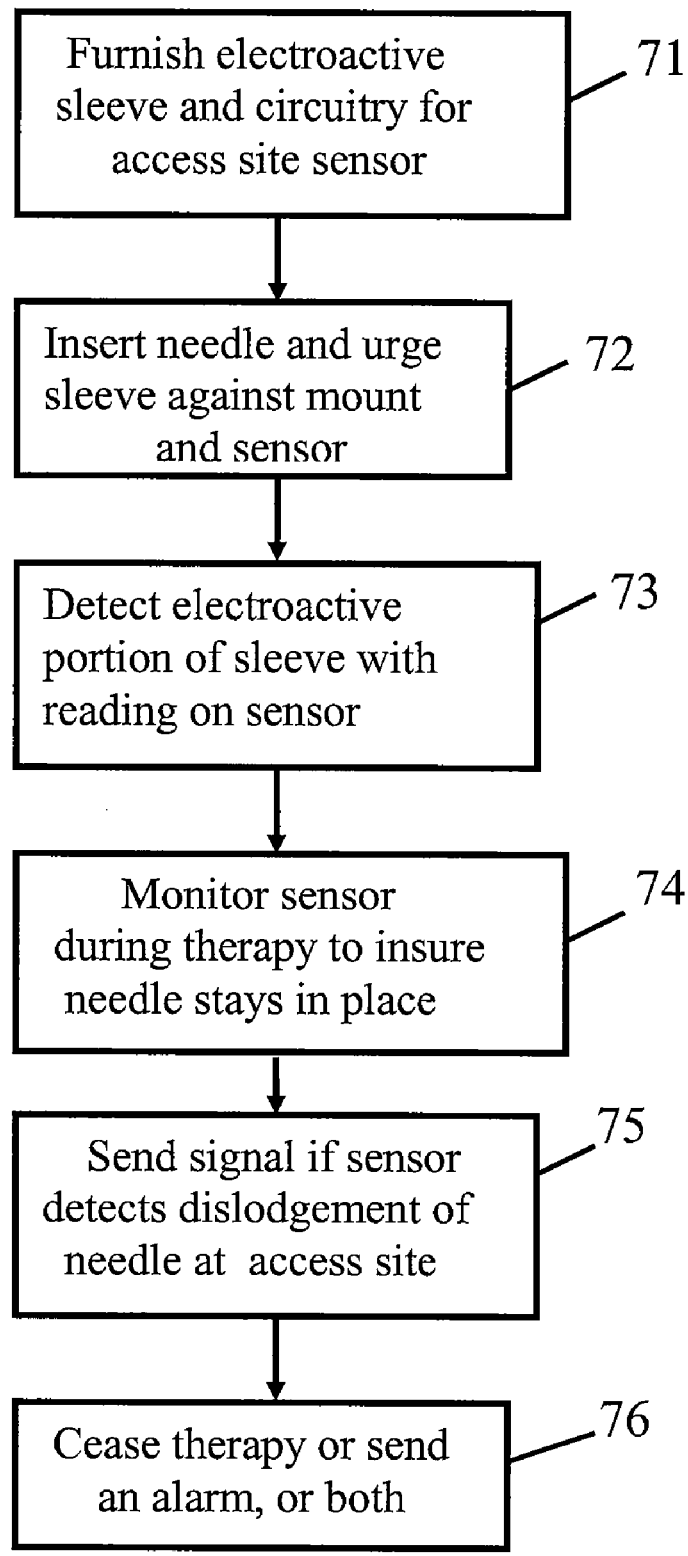
FIG. 7 is a flowchart for a method of using the sensor and electroactive sleeve.

Among the embodiments are included methods for using a sleeve with an electrical or magnetic element. A flowchart for one method is depicted in FIG. 7. In this method, an access needle is furnished 71, the access needle having an electroactive sleeve and circuitry for detecting the active element in the sleeve. To begin the therapy, the needle is inserted 72 into an access site, and the sleeve is rolled up against the needle mount, thus urging the sleeve and the electroactive element against the sensor. The sensor then detects 73 the electroactive element. As noted, the electroactive element may be a metal, a magnet, or an electromagnetic element. The sensor is a device that detects a metallic or magnetic device. The sensor may be a hall-effect sensor or a proximity sensor, such as a capacitive or inductive sensor.

While therapy continues, the sensor is monitored 74 to insure that the needle is not dislodged from the access site. If the needle is dislodged, the sleeve will unroll, moving the piece of metal or magnet away from the sensor. The sensor reading will change and the control circuitry will send a signal 75 indicating that there has been a dislodgement of the needle from the access site. The therapy machine may then be programmed to cease therapy 76, e.g., cease pumping blood from the patient, or to take some other action, such as sending an alert to the patient or a caregiver, or to sound an alarm. There are may other embodiments for use of an electroactive sleeve and a sensor.

Figure 8:
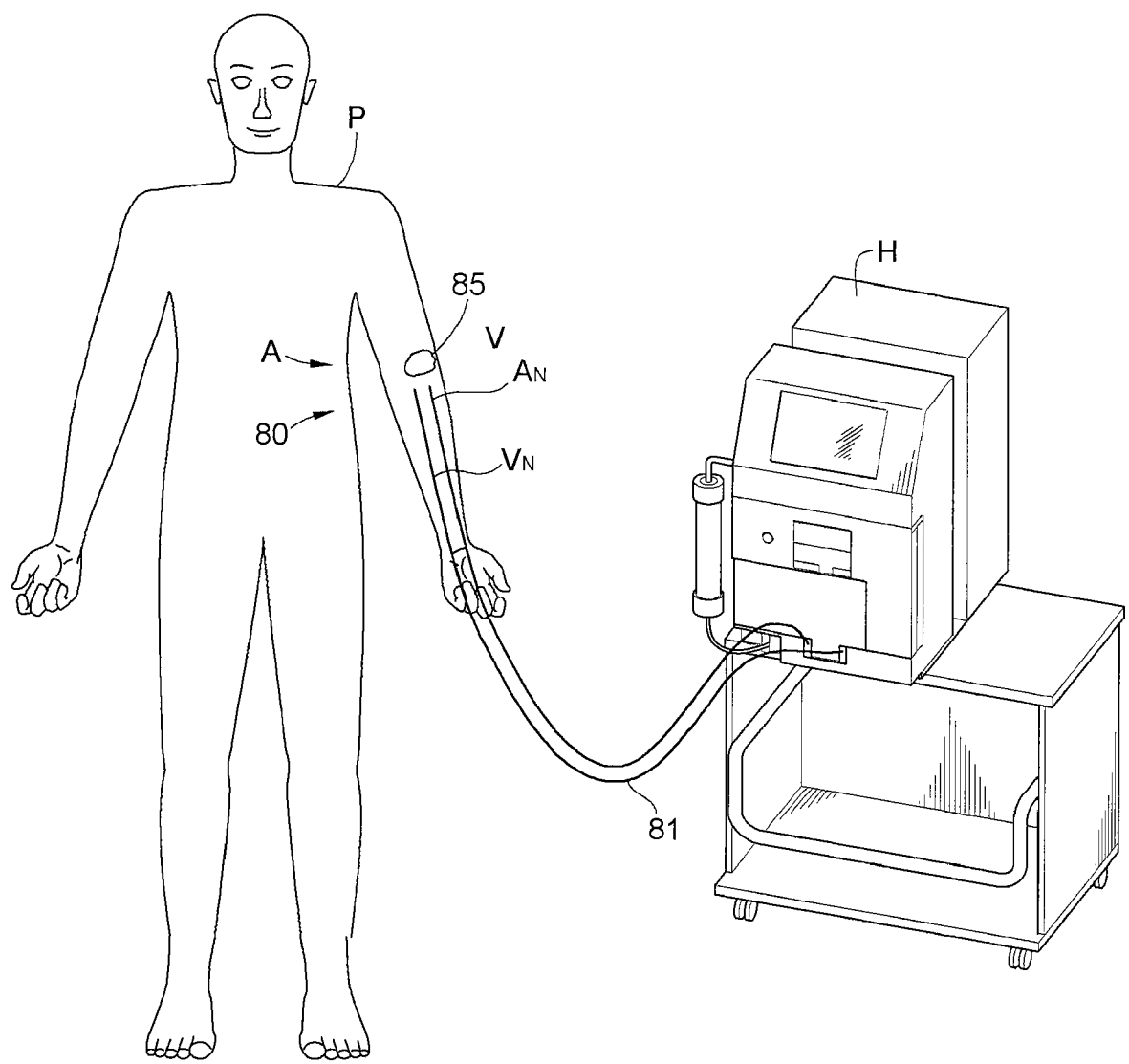
FIG. 8 is a hemodialysis machine with a needle dislodgement circuit that includes a sensor and an electroactive sleeve.

FIG. 8 depicts a patient undergoing therapy with a hemodialysis machine H and the needle dislodgement system 80. The patient is connected to the hemodialysis machine via blood lines 81, which are used with arterial access site A and access needle $A_n$ and venous access site V and venous needle $V_n$. The venous access needle $V_n$ includes a needle with a mount and a sensor on the mount, as described in any of the embodiments above. The needle also includes a sleeve with a metallic or magnetic component. The component is large enough to be detected by a sensor on the needle mount, such as a hall-effect or proximity sensor. When the needle is placed on the access site for therapy, the sleeve is rolled up and the sensor detects the component. When the needle is dislodged, the sensor no longer detects the component and an alert or an alarm is given.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method of detecting a needle disconnection, the method comprising:
   providing a needle having a mount with a sensor and a sleeve with a metallic target, the sensor configured for detecting the metallic target;
   placing the needle into an extracorporeal blood processing access site;
   urging the sleeve against the mount, thereby placing at least a portion of the metallic target near the sensor;
   taking a reading of the sensor after the metallic target is urged against the mount;
   monitoring the access site by taking additional readings of the sensor during an extracorporeal blood processing therapy; and
   sending a signal if a reading consistent with absence of the target from the sensor is detected, thereby indicating dislodgement of the needle.

2. The method of claim 1, further comprising taking a baseline reading of the sensor before the step of urging the sleeve against the mount.

3. The method of claim 1, wherein the signal is sent to a local output device to alert a person or to sound an alarm.

4. The method of claim 1, wherein the sensor is a hall-effect sensor or a proximity sensor.

5. A method for detecting needle disconnection at an access site, the method comprising:
   providing an access needle with an electroactive sleeve and a sensor on a mount of the access needle, wherein the sensor is configured to detect metal or a magnet on the sleeve;
   mounting the access needle on the access site of a patient and pressing the sleeve toward the mount;
   taking a reading of the sensor with the pressed sleeve;
   monitoring the access site during a therapy procedure by taking additional readings with the sensor; and
   sending a signal if a reading indicative of needle dislodgement is taken.

6. The method of claim 5, further comprising taking a first baseline reading of the sensor and the sleeve while the sleeve covers the needle, and saving data of the first baseline reading for comparison with the baseline reading.

7. The method of claim 5, further comprising sending a local alert as a result of sending the signal.

8. The method of claim 5, further comprising saving data of the reading.

9. A system for detecting needle dislodgement, the system comprising:
   an access needle suitable for mounting near an access site for extracorporeal therapeutic blood processing, the access needle including a mount;
   a sleeve having an electromagnetic target, the sleeve positioned over the needle and adjacent the mount;
   a sensor on the mount for detecting the electromagnetic element; and
   a communications circuit in communication with the sensor, wherein the needle is configured for placing into the access site, the sleeve is configured for pressing against the mount, the sensor is configured for detecting the electromagnetic element, and the communications circuit is configured for sending data indicative of a position of the electromagnetic element with respect to the sensor.

10. The system according to claim 9, wherein the electromagnetic target is selected from the group consisting of magnet or a piece of metal placed on a distal end of the sleeve, and metallic or magnet wire embedded within the sleeve.

11. The system according to claim 9, wherein the sensor is selected from the group consisting of a hall-effect sensor, a proximity sensor, and a magnetic sensor.

12. The system according to claim 9, wherein the sleeve has a shape of a thin tube or bellows.

13. A system for detecting needle dislodgement, the system comprising:
   a needle with a mount suitable for mounting near an access site for an extracorporeal blood therapy;
   a sleeve having a metallic or magnetic target, the sleeve positioned over the needle and adjacent the mount;
   a sensor on the mount for detecting the metallic or magnetic target; and
   a control circuit connected to the sensor, wherein the needle is configured for placing into the access site, the sleeve is configured for pressing against the mount, and the control circuit is configured for taking readings of the sensor indicative of a position of the metallic or magnetic target with respect to the sensor.

14. The system according to claim 13, further comprising a local output device selected from the group consisting of a video screen and a speaker.

15. The system according to claim 13, further comprising a hemodialysis machine for providing the extracorporeal therapy.

16. The system according to claim 13, wherein the sleeve comprises a bellows made from a thin plastic or elastomeric material.

17. The system according to claim 13, wherein the metallic or magnetic target is positioned near a distal end of the sleeve.

18. The system according to claim 13, wherein a shape of the metallic or magnetic target is selected from the group consisting of a thin cylinder or an arc.

19. The system according to claim 13, wherein the sensor is a hall-effect sensor, a capacitance sensor, an inductance sensor, or a magnet sensor.

* * * * *